United States Patent [19]

Sigworth

[11] Patent Number: 5,495,746
[45] Date of Patent: *Mar. 5, 1996

[54] GAS ANALYZER FOR MOLTEN METALS

[76] Inventor: Geoffrey K. Sigworth, 321 Tioga St., Johnstown, Pa. 15905

[*] Notice: The term of this patent shall not extend beyond the expiration date of Pat. No. 5,345,808.

[21] Appl. No.: 276,457

[22] Filed: Jul. 18, 1994

Related U.S. Application Data

[63] Continuation-in-part of Ser. No. 113,344, Aug. 30, 1993, Pat. No. 5,345,808.

[51] Int. Cl.$^6$ ........................................... G01N 7/10
[52] U.S. Cl. ................................ 73/19.07; 73/19.1
[58] Field of Search .................................. 73/19.01, 19.07

[56] References Cited

U.S. PATENT DOCUMENTS

| | | |
|---|---|---|
| 2,861,450 | 11/1958 | Ransley . |
| 4,239,532 | 12/1980 | Allersma et al. . |
| 4,454,748 | 6/1984 | Terai et al. . |
| 4,624,128 | 11/1986 | Pelton . |
| 4,757,707 | 7/1988 | Harvey et al. . |
| 4,878,375 | 11/1989 | Roggen . |
| 4,907,440 | 3/1990 | Martin et al. . |
| 5,345,808 | 9/1994 | Sigworth ................................ 73/19.07 |

FOREIGN PATENT DOCUMENTS

| | | |
|---|---|---|
| 435365 | 3/1991 | European Pat. Off. . |

OTHER PUBLICATIONS

Ramsley et al., "An Instrument for Measuring the Gas Content of Aluminum Alloys During Melting and Casting", Journal of the Institute of Metals, 1957–58, vol. 86, pp. 212–219.

E. Fromm, "Determination of the Hydrogen Concentration in Aluminum Melts by Continuous Measurements of the Hydrogen Equilibrium Pressure", Aluminum, 65 (1989). No. 12, pp. 1240–1243.

*Primary Examiner*—Hezron E. Williams
*Assistant Examiner*—Jay L. Politzer
*Attorney, Agent, or Firm*—Andrew Alexander

[57] ABSTRACT

Disclosed is a probe for determining the gas content of molten metal. The probe comprises a porous filter head permeable to gas and impermeable to the molten metal and a small diameter tube having an upper portion and a lower portion, the tube attached to the filter head at the lower portion. A device for drawing a vacuum on the tube and a device for measuring gas pressure in the tube is provided.

11 Claims, 2 Drawing Sheets

GAS ANALYZER FOR MOLTEN METALS

CROSS REFERENCE TO RELATED APPLICATIONS

This application is a continuation-in-part of U.S. Ser. No. 08/113,344, filed Aug. 30, 1993 and now U.S. Pat. No. 5,345,808.

INTRODUCTION

This invention relates to molten metals, and more particularly, it relates to an apparatus and method for the direct measurement of the level of gas in a molten metal.

There has been a great interest in accurately determining the level of gas dissolved in a molten metal because dissolved gas can result in the formation of holes or cracks in the ingot cast therefrom. In aluminum, for example, hydrogen has a much greater solubility in the molten metal than in the solid form. That is, hydrogen is almost twenty times more soluble in molten aluminum than in solid aluminum. Thus, when molten aluminum freezes gas present in the melt prior to solidification is rejected by the solid and accumulates in the remaining liquid until the concentration of dissolved gas becomes sufficiently large to form gas bubbles or pores. Because of this problem, it is important to be able to accurately and quickly determine the level of hydrogen dissolved in the molten aluminum, and whether further degassing is necessary. In addition, it is important to know when the level of hydrogen has reached an acceptable level in order to optimize the casting process, and avoid unnecessary costs associated with casting.

Many methods have been suggested and tried to measure the level of gases in molten metal. However, these methods are either too time consuming or they utilized equipment which is too fragile. It will be understood that it is important to obtain the results of the gas measurement quickly, accurately and continuously in order to maintain control of the degassing process. Further, it will be understood that fragile equipment merely leads to erroneous results.

There are two general methods for measuring dissolved gas in molten metal. In the first of these methods, a stream of inert gas is introduced into and collected from the molten metal. This gas stream is recirculated by pumping many times through the metal until the partial pressure of dissolved gas in the recirculating inert gas bubbles is the same as the partial pressure of dissolved gas in the liquid metal. This technique is described in detail by Ransley in U.S. Pat. No. 2,861,450. However, this method tends to be cumbersome and slow, and the equipment required for recirculating the inert gas is costly. Various improvements have been proposed for this method of analysis (see U.S. Pat. Nos. 4,454,748, 4,624,128, 4,757,707, and 4,907,440) but they still do not solve all the problems inherent in this procedure.

The second method, referred to herein as the direct pressure measurement method, does not use recirculating gas bubbles, but instead utilizes a probe having a porous tip which permits dissolved gas to pass through but does not permit molten metal to pass. This method was disclosed by C. E. Ransley, et al. in an article entitled "An Instrument for Measuring the Gas Content of Aluminum During Melting and Casting of Aluminum" published in the Journal of the Institute of Metals, Vol. 86, pp. 212–219 (1957–1958). Ransley et al. showed that the direct pressure method can give reliable and accurate gas measurements. However, because of the complex diffusion membrane required, it was concluded that the method was not practical. Thus, although established in principle 35 years ago, the direct pressure measurement method of gas analysis has not become a viable commercial technique because of problems associated with the probe assembly that contacts the molten metal.

A direct pressure measurement device is disclosed by E. Fromm in an article entitled "Determination of the Hydrogen Concentration in Aluminum Melts by Continuous Measurement of the Hydrogen Equilibrium Pressure" published in Aluminum Vol. 65, (1989). The article notes that the main problem in building an analyzer is the selection of suitable materials for the part of the probe or sensor submerged in the melt. The probe consists of a tube with a porous tip. The article notes that the tube must not react with the melt or must react only slowly and must be resistant to thermal shock. Further, the article suggests the use of alumina tubes because they have long-term stability and adequate resistance to thermal shock. However, the article notes that the alumina tubes must be handled carefully, particularly when lowered into the hot melt. The article notes that metal tubes are not suitable unless used only briefly.

To create a thermal shock-resistant article, Allersma et al. U.S. Pat. No. 4,239,532 discloses a unitary probe having the porous end thereof formed by leaching. This patent suggests that the probe be fabricated from ceramic composites of mullite and silica or alumina and silica and that the material selected for the probe must be leachable. However, this severely limits the materials that may be employed. Another disadvantage of this probe was the very slow response time.

Roggen U.S. Pat. No. 4,878,375 discloses a probe for measuring hydrogen in aluminum melts, and indicates that the capillary tube is preferably made from alumina. The patent also discloses the use of a graphite porous tip or calcined material not wet by the melt. Roggen also states that metallic capillary tubes, e.g., steel or nickel tubes plasma coated with aluminum oxide, can also be employed, but no practical operating experience was reported for these materials.

EPO 435 365 A1 discloses a probe for measuring hydrogen in molten aluminum. The probe employs a porous aluminum oxide tube that is welded onto the end of a stainless steel tube. A tube of aluminum surrounds the probe. The outer aluminum tube melts upon immersion in the melt. According to the reference, this alleviates thermal shock. According to the inventors, for best results the assembly must be preheated for 24 hours prior to immersion in liquid metal. However, this probe would seem to be costly to produce and inconvenient to use.

It will be seen that there is still a great need for an improved analyzer that employs a probe that is resistant to thermal shock, easy to use, inexpensive to manufacture, and that is rugged and reliable when used on the floor of the casting plant. The present invention provides such a probe.

SUMMARY OF THE INVENTION

It is an object of the invention to provide an improved gas analyzer for molten metal.

It is another object of the invention to provide an improved gas analyzer to determine the amount of hydrogen dissolved in molten aluminum.

It is still another object of the invention to provide an improved analyzer which utilizes a probe comprised of a combination metal tube and porous filter member.

Still, it is another object of the invention to provide an improved analyzer which utilizes a probe comprised of a steel or stainless steel tube and a porous filter member.

And still, it is another object of the invention to provide an improved analyzer which utilizes a probe comprised of a steel or stainless steel tube having a protective coating thereon resistant to attack by molten metal and a porous member on one end thereof permeable by gas and impervious to molten metal.

These and other objects will become apparent from a reading of the specification and claims appended hereto.

In accordance with these objects, there is provided a hollow probe for immersion in a molten metal for determining the gas content thereof by drawing a vacuum on the probe and permitting gas to permeate from the molten metal and equilibrate in the probe, wherein gas pressure can be measured to determine the gas pressure in the molten metal. The probe comprises a porous filter head permeable to gas and impermeable to the molten metal, and a hollow steel tube or stainless steel tube having an upper portion and a lower portion, the tube attached to the filter head at the lower portion. The tube employed has a lower portion which connects to the filter head and another or upper end attached to means for drawing a vacuum on the tube and means for measuring gas pressure in the tube.

DETAILED DESCRIPTION OF PREFERRED EMBODIMENTS

Figure 1:
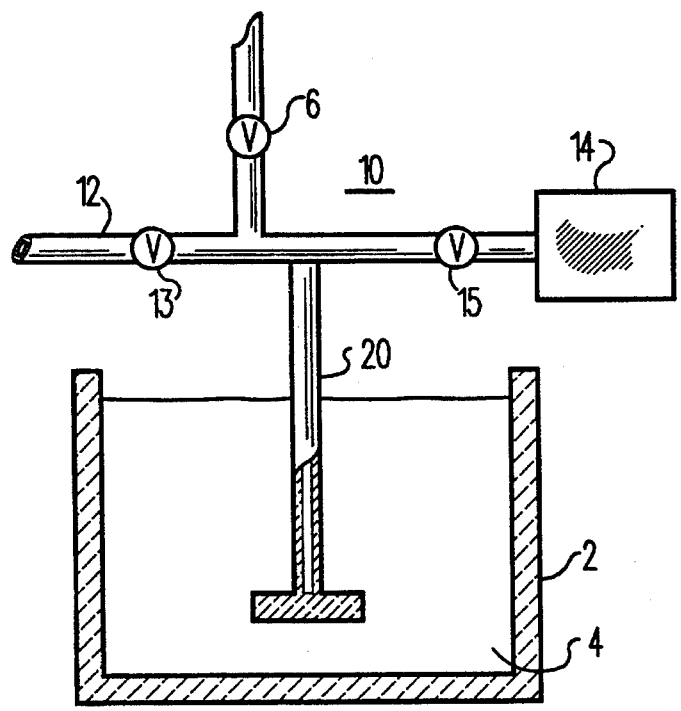
FIG. 1 is a schematic of a gas analyzer in accordance with the invention.

Referring now to FIG. 1, there is shown a schematic of an analyzer 10 having a probe 20 provided in a tank 2 of molten metal 4. Further, the analyzer comprises a vacuum means 12 and gas pressure analysis means 14. Means 6 can be provided for doping probe 20 to improve gas diffusion response time. The molten metal for which the analyzer is used can be any molten metal where it is desired to determine the amount of gas, such as hydrogen, nitrogen or oxygen, in the molten metal. In general, a vacuum is applied to the probe 20 and the valve 13 is closed, after which a period of time is allowed for gas in the molten metal to diffuse through the porous filter head into the probe until equilibrium is reached. Then, the level of gas from the melt is measured by the gas pressure analysis means 14. In this way, the level of gas in the molten metal is determined.

Figure 2:
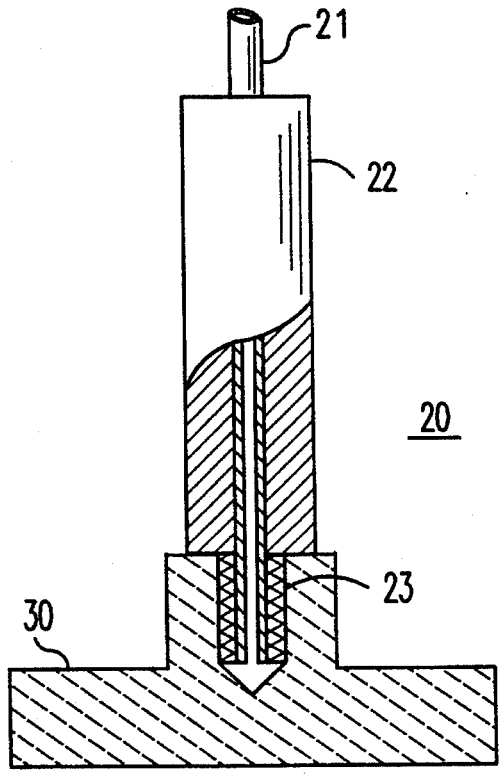
FIG. 2 is a cross-sectional view of one embodiment of the probe.

In FIG. 2, there is shown a probe 20 in accordance with the invention. The probe is comprised of a filter head 30, a small diameter steel or stainless steel tube 21 which is covered with a protective refractory sleeve 22. The sleeve 22 prevents attack of the tube 21 by liquid metal. A second coating 23 may be provided at the lower end of the tube where it joins the filter head 30 to prevent chemical reaction between the tube 21 and the filter head 30.

Figure 3:
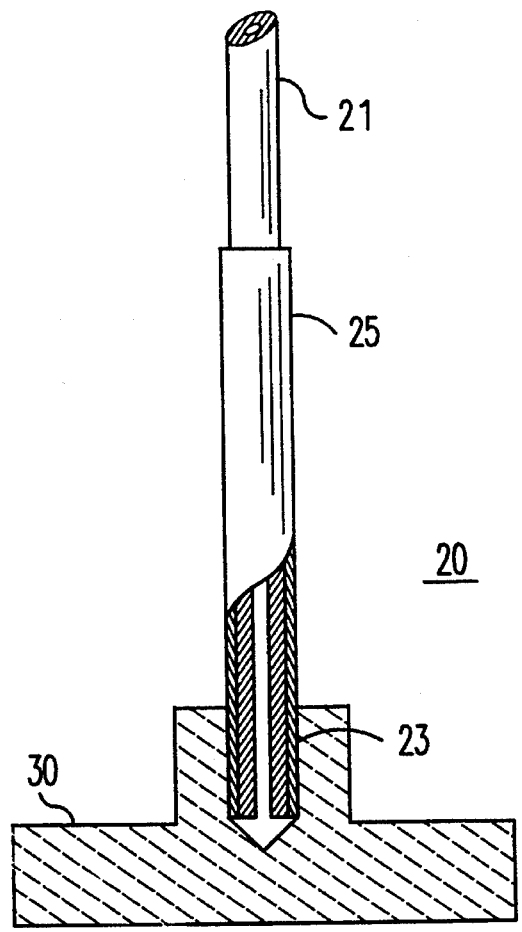
FIG. 3 is a cross-sectional view of a second embodiment of the probe.

In FIG. 3, there is shown another embodiment of the probe 20 in accordance with the invention. The probe is comprised of a filter head 30, a small diameter steel or stainless steel tube 21 which is covered with a protective refractory sleeve 25. The sleeve 25 covers the entire lower end of the tube and prevents both dissolution of the tube by liquid metal and chemical reaction between the tube 21 and the filter head 30 at the lower portion of the tube 23.

The filter head 30 can be fabricated from a material selected from porous carbon, silicon nitride, titanium diboride, silicon carbide, alumina, zirconia, titania and mullite. By reference to carbon herein is meant to include all types of carbon which can be formed into a porous filter head, including graphite. The porous filter head is required to permit diffusion of gas from the molten metal, yet it must be impervious to the molten metal even when a vacuum as low as 1 Torr is imposed on the filter head. For purposes of determining the amount of hydrogen in molten aluminum, it is preferred that the porous filter head be comprised of carbon.

For purposes of the present invention, the filter head can have a cylindrical collar 34 whose thickness is sufficient to provide good mechanical strength to the upper portion 37 of the filter. The filter head may have a flange section 32, preferably circular in shape, extending beyond the periphery of the cylindrical collar 34. The flange has the advantage that it provides greater surface area for contact with the molten metal and thus provides a greater surface area for the gas to diffuse from the molten metal into the probe. This permits the amount of gas in the melt to be determined in a matter of minutes, for example, in one or two minutes. Thus, the greater surface area of the filter head aids in providing a faster response time for the analyzer.

Figure 4:
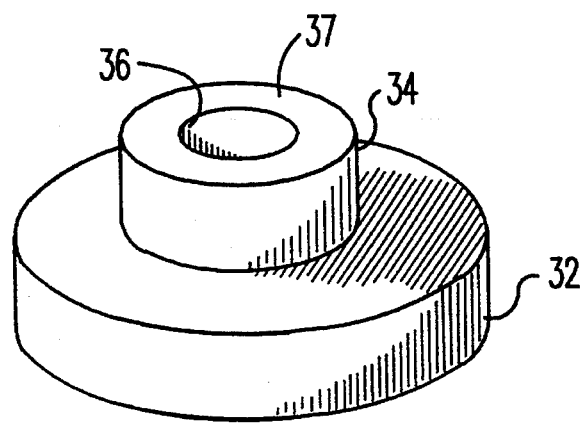
FIG. 4 is a perspective view of an improved porous member.

In the filter head configuration shown in FIG. 4, flange 32 is provided with a collar 34 having an inside cylindrical wall 36 which fits snugly over the bottom portion of protected small diameter tube 23, as shown in FIGS. 2 and 3.

For purposes of providing a connection between filter head 30 and lower portion of the covered tube 23, the lower portion is provided with a diameter approximately the same as the diameter of inside cylindrical wall 36 of collar 34. Both inside cylindrical wall 36 and top 37 of collar 34 should have a finish sufficiently smooth to prevent leakage of molten metal therebetween from the melt. Both lower portion 23 and collar 34 can be machined or fabricated to provide a press fit which prevents leakage.

When the use of the analyzer is, for example, to determine the amount of hydrogen in molten aluminum, it is preferred that the filter head be formed from porous carbon such as porous graphite. Further, sleeve or tube 21 is formed from a stainless steel, such as alloys 316, 304, and 308 or a mild steel such as alloy 1010, and 1018. It is also preferred that tube 21 has its end located or spaced from carbon filter head 32 substantially as shown in FIGS. 2 and 3. The spacing should be an amount or distance sufficient to resist diffusion from the carbon filter head into the steel comprising tube 21. An important embodiment of this invention is the use of a protective coating at the bottom of the tube 23, which prevents the chemical reaction between the carbon filter head and the steel tube to form iron carbide. Thus, the probe assembly has the advantage that it can be used for long times without deterioration of the carbon filter head. In addition, the use of a steel tube 21 provides for a rugged probe which can be used repeatedly without concern for thermal shock and the erroneous reading which can result from leaks developing from the thermal shock.

There are a number of materials which may be used for the protective coating at the bottom of the tube 23, and which will prevent the chemical reaction between the carbon filter head and the steel tube to form iron carbide. The material must satisfy three criteria. It must first be chemically inert to the carbon filter member. That is, it must not be decomposed by the carbon, and it must not form a carbide phase at the temperature of use. Secondly, it must not react with the steel or stainless steel tube. And thirdly, it must not dissolve an appreciable amount of carbon, or the carbon will diffuse through the material and thereby react with the steel tube. Ceramic coatings suitable for this purpose may consist of alumina, silicon nitride, titanium diboride, zirconia, titania, mullite or a combination of these materials. Because carbon has very low solubility in nickel and copper, these materials may also serve as a diffusion barrier between the carbon filter head and the steel or stainless steel tube.

Copper is another metal that may be used for small diameter tube 21.

For purposes of the present invention, in order to minimize response time, it is preferred that small diameter tube 21 have an inside diameter in the range of 0.010 to 0.080 inch. Typically, the small diameter tube has an outside diameter in the range of 0.05 to 0.25 inch.

When the analyzer is used to measure gases in certain molten metals, such as magnesium, for example, the steel or stainless steel tube is resistant to attack by the molten metal. However, in certain melts, such as molten aluminum, the steel can be attacked by the melt. Thus, in a preferred embodiment, a ceramic coating 22 and 25 is applied to the steel tube. A ceramic coating is chosen that can withstand attack by the particular melt in which it is used. For example, if the analyzer is to be used with molten aluminum, then the steel tube should be provided with a protective coating of ceramic or vitreous enamel. The ceramic coating suitable for use in molten aluminum is selected from alumina, silicon nitride, titanium diboride, silicon carbide, zirconia, titania, mullite or a combination of these materials. The coatings may be applied by means which provides a continuous coating that adheres to the surface of the tube. Fluxes or additions to lower the melting point of the ceramic may also be incorporated into the coating. For example, such coatings may be applied as a slurry coating and then baked to produce the ceramic outer coating resistant to the molten aluminum. One such coating which can be used in accordance with the invention is available from Consolidated Ceramics Products, Inc., 838 Cherry Street, Blanchester, Ohio 45107. The thickness of the coating can range from 0.003 to 0.05 inch. As many of these coatings are chemically stable in contact with carbon, they may serve to prevent the chemical reaction between the carbon filter head and a steel tube as shown in FIG. 3.

In another embodiment of the invention a castable or moldable ceramic 22 of the aforementioned ceramic materials may be applied to the surface of the tube to prevent attack by molten metal.

In the invention, the small diameter tube is connected to vacuum system 12.

In operation, the probe is lowered into the melt and then a vacuum is drawn on the small diameter tube by vacuum means 12. The vacuum is drawn to a low level, e.g. less than about 0.5 Torr. The vacuum removes any gas present inside the small diameter tubing and inside the pores of the filter head. When molten aluminum is being tested and the porous filter head is graphite, a vacuum of 0.5 Torr is suitable. Then, the vacuum means is turned off and valve 13 is closed to maintain a constant volume inside the evacuated measuring system. After the gas in the melt reaches equilibrium in the small diameter tube or constant volume measuring system, the gas pressure in the small diameter tube is measured. The pressure can be measured by means of a pressure transducer. A suitable transducer is available from Barksdale Controls Division of IMO Industries, 3211 Fruitland Ave., Los Angeles, Calif. 90058. However, other pressure measuring devices can be used, including ion pumps, vacuum gauges, etc.

In another aspect of the invention, a process has been developed for greatly shortening the time required to determine the level of gas pressure in molten metal. In accordance with this aspect of the invention, when the probe is first immersed in molten metal, an instantaneous gas pressure, P, is obtained and the rate of gas pressure increase with time, dP/dt, in the evacuated probe is obtained. Thereafter, a doping gas is introduced to the probe to artificially increase the gas pressure therein and then the rate of gas pressure increase with time, dP/dt, inside the probe is measured again. This procedure may be repeated a number of times until the equilibrium pressure of the gas in the molten metal is reached. In accordance with this aspect of the invention, the equilibrium pressure can be reached much more quickly because this new method does not require the full time for the gas in the probe to build up from the molten metal. That is, only sufficient time is required to determine whether the equilibrium pressure has been reached. This may be done in one or two measurements or in a series of measurements.

While the invention has been set forth with respect to preferred embodiments, all embodiments are claimed which come within the spirit of the invention.

What is claimed is:

1. A hollow probe for immersion in a molten metal for determining the gas content thereof by drawing a vacuum on the probe and permitting gas to permeate from the molten metal and equilibrate in the probe wherein gas pressure can be measured to determine the gas pressure in the molten metal, the probe comprising:

(a) a porous filter head permeable to gas in said molten metal and impermeable to said molten metal;

(b) a small diameter metal tube having an upper portion and a lower portion, the tube attached to said filter head at the lower portion; and (c) said tube attached at said upper portion to means for drawing a vacuum on said tube and means for measuring gas pressure in said tube.

2. The probe in accordance with claim 1 wherein said small diameter tube has a ceramic coating thereon resistant to attack by molten metal.

3. The probe in accordance with claim 1 wherein said small diameter tube has an inside diameter in the range of 0.01 to 0.08 inch.

4. The probe in accordance with claim 1 wherein said small diameter tube is fabricated from copper.

5. The probe in accordance with claim 1 wherein said small diameter tube is fabricated from steel.

6. The probe in accordance with claim 1 wherein said small diameter tube is fabricated from stainless steel.

7. The probe in accordance with claim 1 wherein said lower portion of said tube has a cylindrical shaped lower section and said filter head has a cylindrical recessed section for fitting snugly to said cylindrical shoulder section.

8. The probe in accordance with claim 1 wherein said porous filter head is fabricated from a material selected from at least one of the group consisting of carbon, silicon nitride, titanium diboride, silicon carbide, alumina, zirconia, titania and mullite.

9. The probe in accordance with claim 1 wherein said porous filter head is fabricated from carbon and said tube is fabricated from steel.

10. The probe in accordance with claim 9 wherein the lower portion of said small diameter tube has a coating which prevents chemical reaction between the small diameter steel tube and the porous carbon filter head.

11. A hollow probe for immersion in a molten metal for determining the gas content thereof by drawing a vacuum on the probe and permitting gas to permeate from the molten metal and equilibrate in the probe wherein gas pressure can be measured to determine the gas pressure in the molten metal, the probe comprising:

(a) a porous carbon filter head permeable to gas in said molten metal and impermeable to said molten metal;

(b) a small diameter steel tube having an upper portion and a lower portion, the tube:

(i) attached to said carbon filter head at the lower portion, and (ii) having at its lower portion a coating that prevents chemical reaction between said steel tube and said porous carbon filter head; and (c) said tube attached at said upper portion to means for drawing a vacuum on said tube and means for measuring gas pressure in said tube.

* * * * *